(12) United States Patent
Blackwell et al.

(10) Patent No.: US 8,177,846 B2
(45) Date of Patent: May 15, 2012

(54) END CAP FOR A VERTEBRAL IMPLANT

(75) Inventors: Jonathan Blackwell, Arlington, TN (US); Thomas E. Drochner, Memphis, TN (US); Michael J. Merves, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 294 days.

(21) Appl. No.: 12/604,177

(22) Filed: Oct. 22, 2009

(65) Prior Publication Data
US 2011/0098820 A1   Apr. 28, 2011

(51) Int. Cl.
*A61F 2/44* (2006.01)
(52) U.S. Cl. .................................................. 623/17.16
(58) Field of Classification Search .... 623/17.11–17.16; 606/280–283
See application file for complete search history.

(56) References Cited

U.S. PATENT DOCUMENTS

| | | | |
|---|---|---|---|
| 4,657,550 A | 4/1987 | Daher | |
| 7,488,330 B2* | 2/2009 | Stad | 606/102 |
| 2007/0255408 A1 | 11/2007 | Castleman et al. | |
| 2007/0255409 A1* | 11/2007 | Dickson et al. | 623/17.11 |
| 2008/0114467 A1* | 5/2008 | Capote et al. | 623/23.47 |
| 2008/0177387 A1* | 7/2008 | Parimore et al. | 623/17.16 |
| 2009/0112325 A1* | 4/2009 | Refai et al. | 623/17.16 |
| 2009/0138089 A1 | 5/2009 | Doubler et al. | |

FOREIGN PATENT DOCUMENTS

| | | |
|---|---|---|
| WO | 2000049977 A1 | 8/2000 |
| WO | 2007127580 A1 | 11/2007 |

OTHER PUBLICATIONS

International Searching Authority, International Search Report and Written Opinion, Jun. 20, 2011.

* cited by examiner

*Primary Examiner* — Eduardo C Robert
*Assistant Examiner* — James Palmer (57) ABSTRACT

An implant for insertion between adjacent vertebral members, comprising an implant body with at least one base section and an end cap. The end cap is adapted for selective positioning on a base section via rotational adjustment of the end cap. The end cap comprises an exterior contact surface that faces away from the implant body when positioned on the base section, a seating surface which contacts the base section when positioned on the implant body, an end cap angulation, and locking passages extending between the exterior contact surface and seating surface and adapted to receive base section teeth. The locking passages and base teeth are complimentarily configured to engage and securely maintain the end cap positioned on the base section such that the implant imparts the end cap angulation to an adjacent vertebral body at a selected point when the implant is positioned between adjacent vertebral members.

17 Claims, 7 Drawing Sheets

END CAP FOR A VERTEBRAL IMPLANT

BACKGROUND

The present application is directed to implants, devices and methods for stabilizing vertebral members, and more particularly, to intervertebral implants, devices and methods of use in replacing an intervertebral disc, a vertebral member, or a combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

As is known, various conditions and ailments may lead to damage of the spine, intervertebral discs and/or the vertebral members. The damage may result from a variety of causes including, but not limited to, events such as trauma, a degenerative condition, a tumor, or infection. Damage to the intervertebral discs and vertebral members can lead to pain, neurological deficit, and/or loss of motion.

Various procedures include replacing a section of or the entire vertebral member, a section of or the entire intervertebral disc, or both. One or more replacement implants may be inserted to replace the damaged vertebral members and/or discs. The implants are configured to be inserted into the intervertebral space and contact against adjacent vertebral members. The implants are intended to reduce or eliminate the pain and neurological deficit, and increase the range of motion.

The curvature of the spine and general shapes of the vertebral members may make it difficult for the implants to adequately contact the adjacent vertebral members or to position the adjacent vertebral members in a desired orientation. There is thus a need for implants or devices configurable to match the spinal anatomy for secure contact and/or desired orientation when implanted into an intervertebral space.

SUMMARY

The present application discloses implants or devices for insertion into an intervertebral space between first and second vertebral members. The implants may include an implant body with first and second base sections with base teeth. An end cap may be connected to the implant body and include an exterior contact surface that faces away from the implant body when the end cap is positioned on the base section, a seating surface adapted to contact the base section when the end cap is positioned on the implant body, an end cap angulation, and locking passages extending between the exterior contact surface and the seating surface and adapted to receive base teeth. A locking passage and base teeth locking mechanism may connect the end cap and the body for the end cap to substantially lock the end cap to the implant body and impart a desired angular position to an adjacent first or second vertebral member. The body and the end cap each include locking passages that permit the end cap to lock onto the implant body, and impart a desired angular position to an adjacent first or second vertebral member when the implant is positioned in the intervertebral space. The locking passages may be configured and located to permit rotational end cap adjustment to position the end cap in selected position relative to the implant body in order to thereby impart a desired angular position at a desired point to an adjacent first or second vertebral member when the implant is positioned in the intervertebral space.

An implant for insertion into an intervertebral space between a first and second vertebral member. The implant comprising an implant body with at least one base section with base teeth, and an end cap. The end cap adapted for selective positioning at a selected point on a base section. The end cap comprising an exterior contact surface that faces away from the implant body when the end cap is positioned on the base section, a seating surface adapted to contact the base section when the end cap is positioned on the implant body, an end cap angulation, and locking passages extending between the exterior contact surface and the seating surface and adapted to receive base teeth. The locking passages and base teeth are complimentarily configured to engage and securely maintain the end cap positioned on the base section such that the implant imparts the end cap angulation to an adjacent vertebral body at the selected point when the implant is positioned in the intervertebral space. The end cap is further selectively positioned on the base section via rotational adjustment of the end cap about an implant longitudinal axis so that the end cap angulation coincides to the selected point.

There is also provided an end cap adapted for use with an implant having an implant body with at least one base section and base teeth. The end cap comprising an exterior contact surface including end cap teeth extending away from the exterior contact surface. A seating surface adapted to contact the base section when the end cap is positioned on the implant body. A substantially vertical exterior cap wall extending between the exterior contact surface and the seating surface. A plurality of locking passages extending from the seating surface into the end cap toward the exterior contact surface and adapted to receive the base teeth. The locking passages are configured to receive complimentarily configured base teeth to thereby engage and securely maintain the end cap positioned on the base section of the implant. The locking passages enable the end cap to be selectively positioned at a selected point on the implant base section to thereby impart an end cap angulation to the adjacent vertebral body at the selected point when the implant is positioned in an intervertebral space. The end cap also comprises an end cap height measured relative to the seating surface which enables the end cap positioned on the implant to both impart end cap height and the end cap angulation to the adjacent vertebral body at the selected point. The end cap is selectively positionable on the base section via rotational adjustment of the end cap about an implant longitudinal axis so that the end cap angulation coincides to the selected point.

The various aspects of the various embodiments may be used alone or in any combination, as is desired.

DETAILED DESCRIPTION

Figure 1:
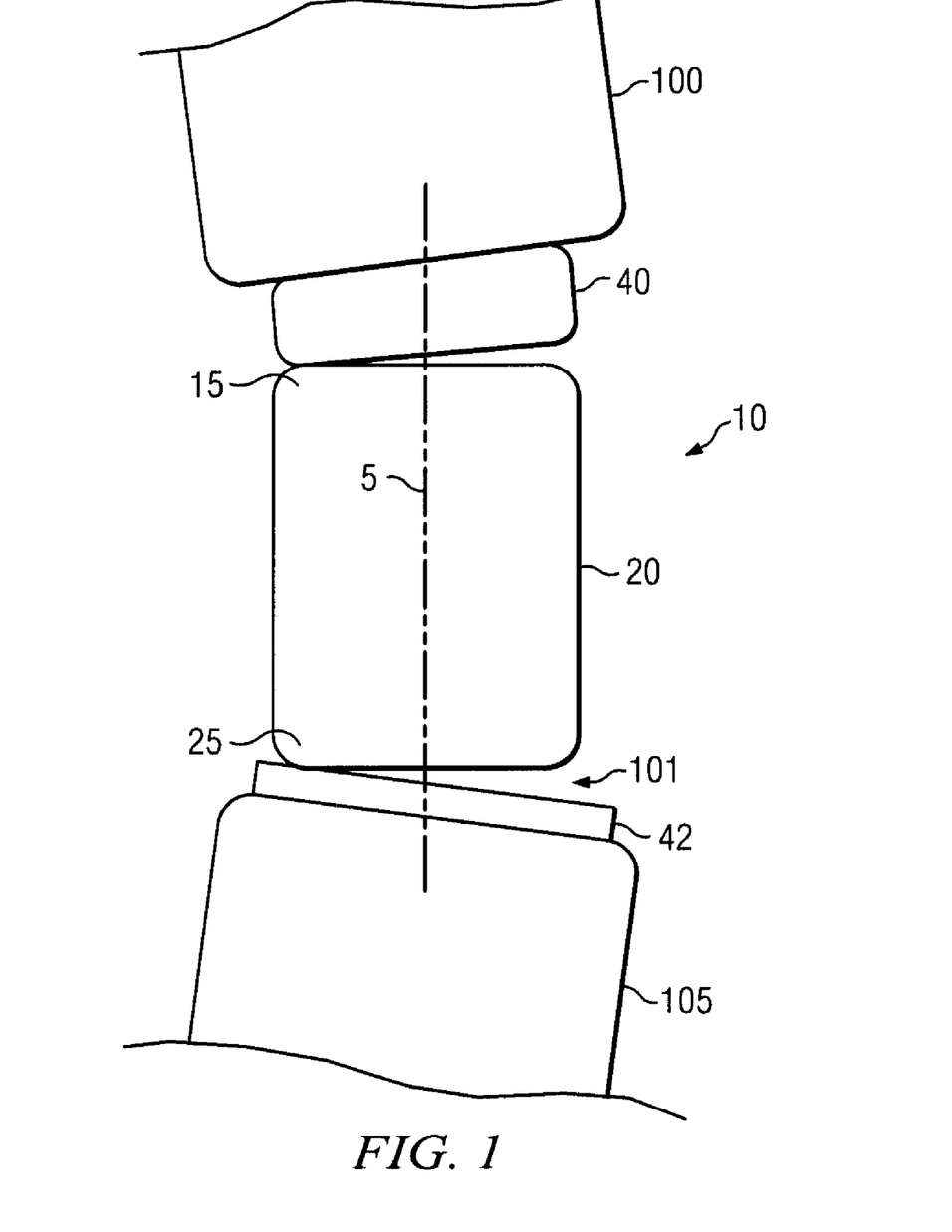
FIG. 1 is a view of an implant positioned between vertebral members according to one embodiment.

The present application is directed to intervertebral implants for spacing apart vertebral members 100 and 105. FIG. 1 shows an implant 10 positioned within an intervertebral space 101 formed between vertebral members 100 and 105. The implant 10 includes an implant body 20 and one or more end caps 40 and 42 attached to the implant body 20 at a first or second implant base section 15 and 25. The one or more end caps 40 and 42 will connect to the implant body 20 to impart a desired angulation θ (shown in FIG. 3B) to impart an angular orientation and/or position to an adjacent vertebral member 100 or 105. A connection or locking mechanism 50, shown in one embodiment in FIG. 3B as a taper locking mechanism, may connect an end cap 40 and 42 to the base section 15 and 25 to improve the contact and stability of the intervertebral implant 10 with the vertebral members 100 and 105 and drive angular orientation for correction or improved alignment of the spine.

As shown in FIG. 1, the implant 10 may include first and second end caps 40 and 42 positioned at opposite ends of the implant body 20 at first and second base sections 15 and 25. The first and second end caps 40 or 42 may have the same or different configuration, height H, and/or the same or different end cap angulation θ. For example, as shown in FIGS. 2B & 2C, one end cap 40 has an angulation θ of 15° degrees and a second end cap 42 has an angulation θ of zero degrees and an end cap height H. Those of skill in the art will recognize that one or two end caps 40 or 42 may be used during a medical procedure with the implant 10 to impart desired or needed height H and angulation θ of adjacent vertebral members 100 or 105 and to correct, improve and stabilize the affected spinal anatomy.

Figure 2A:
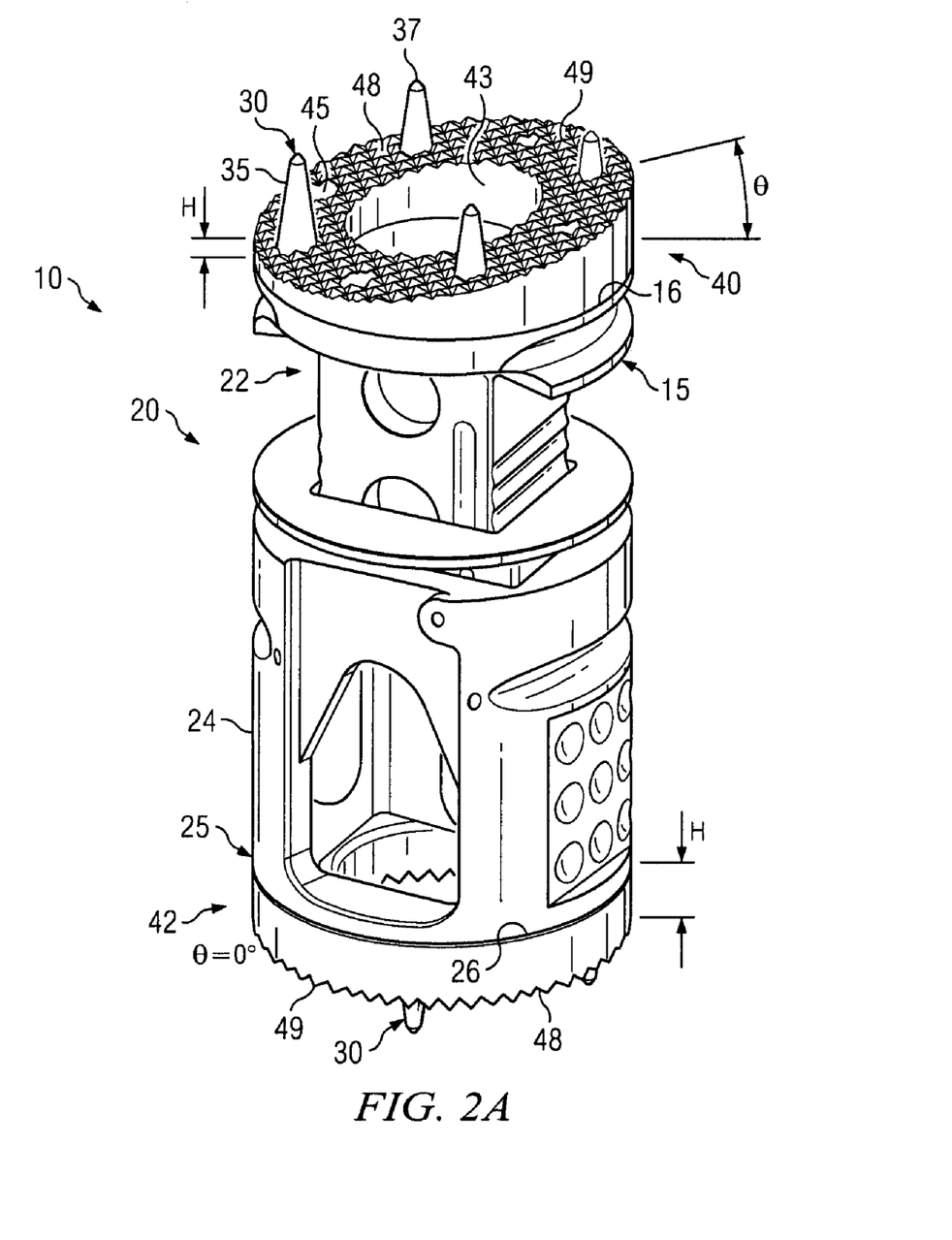
FIG. 2A is a perspective view of an implant with end caps according to one embodiment.
Figure 2B:
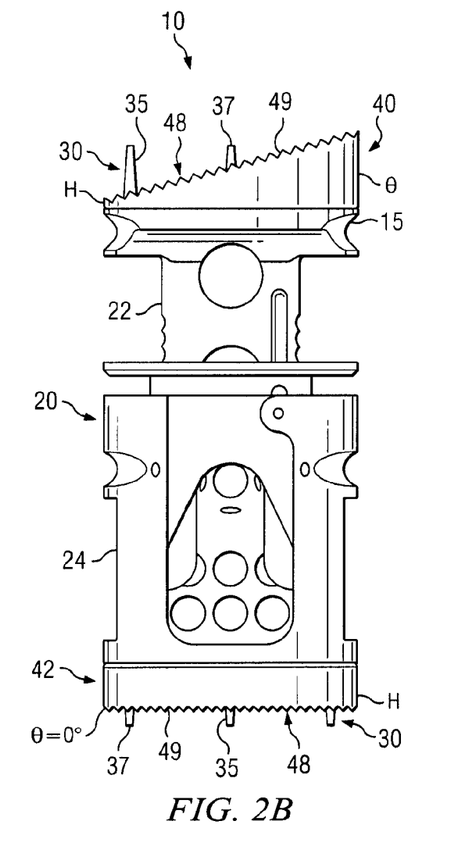
FIG. 2B is a side view of an implant with an end caps according to one embodiment.
Figure 2C:
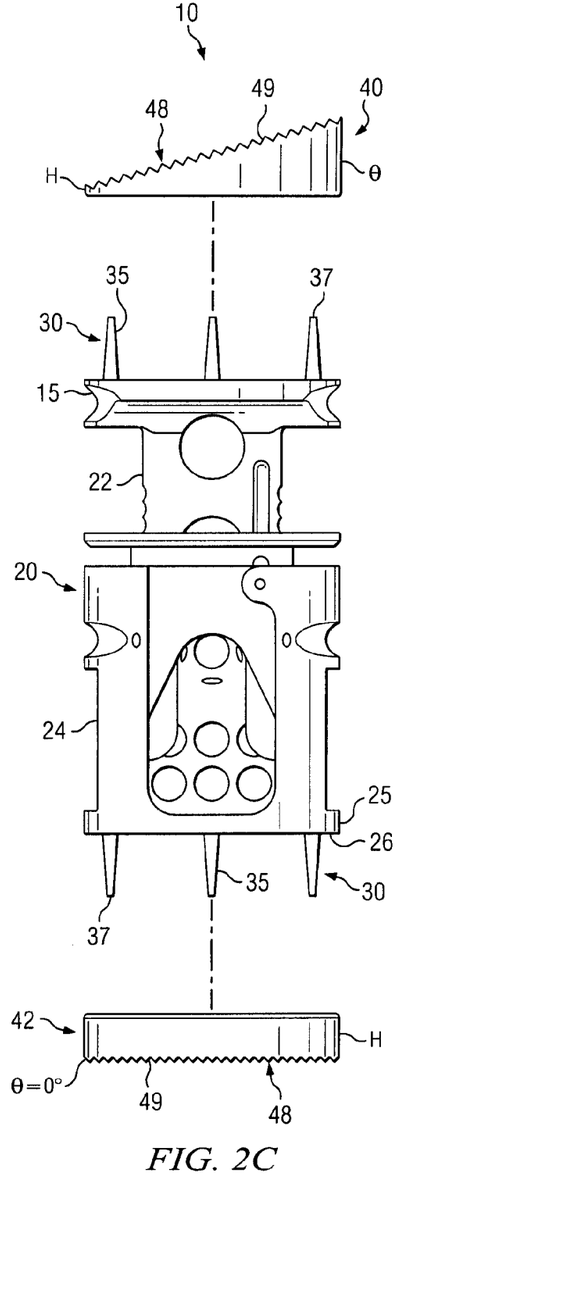
FIG. 2C is an exploded side view of FIG. 2B illustrating an implant with end caps according to one embodiment.
Figure 2D:
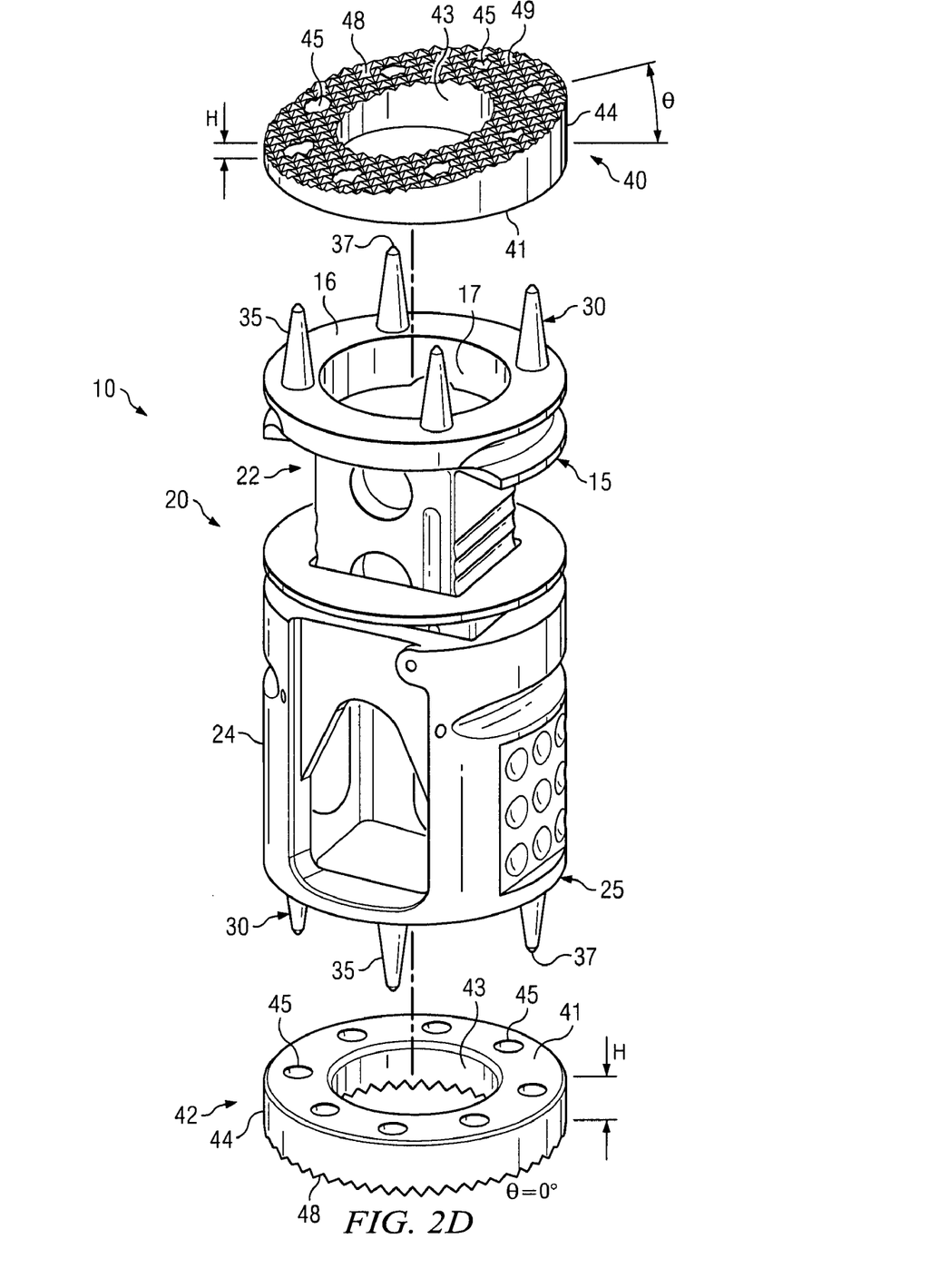
FIG. 2D is an exploded perspective view of FIG. 2A.

FIGS. 2A and 2D show an assembled and exploded perspective view of an implant 10 with upper and lower end caps 40 and 42 according to one embodiment. FIGS. 2B and 2C show an assembled and explode side view of the implant 10 with upper and lower end caps 40 and 42. In the aspect show in FIGS. 2A-2D, the implant body 20 is constructed of two relatively movable sections 22 and 24 to permit adjustment of the axial height of the implant 10. The implant body 20 includes an inner implant body 22 adapted to axially travel inside an outer implant body 24 to thereby enable selected or controlled collapse and expansion of the implant 10. The outer implant body 24 includes a hollow interior and the inner implant body 22 includes a first base section 15. The inner implant body 22 is sized to fit within and axially travel along the hollow interior of the outer implant body 24 to adjust the height of the implant body 20 along the longitudinal axis 5. Both the inner and outer implant bodies 22 and 24 may be hollow and include one or more apertures to receive bone growth material. Also, one or more apertures may extend through the body 20 walls to the hollow interior. However, the implant body 20 may also be constructed from a single section with a fixed height measured between the first and second base sections 15 and 25.

The implant body 20 is configured to receive the end cap 40 or 42. The inner implant body 22 includes a first base section 15 with base teeth 30, shown in FIG. 3C, which extend away from an exterior surface 16 of the first base section 15 in a substantially vertical or axial direction. The outer implant body 24 includes a second base section 25 with similar base teeth 30 which extend away from an exterior surface 26 of the second base section 25 in a substantially vertical or axial direction. The tooth height 33 of the base teeth 30 extending from the first and second base sections 15 and 25 may be the same or different depending on the needs of a surgeon or surgical procedure or clinical application. In one aspect, the base teeth 30 preferably have a tapered configuration and have a substantially cone or conical shape or configuration, shown in FIG. 3C, and extend past an exterior contact surface 48, shown in FIGS. 3A & 3B. Those of skill in the art will recognize that other shapes and teeth height 33 may be used depending on surgeon need, or procedure or clinical need. For example, in another aspect, the base teeth 30 may have a tapered configuration and a substantially cone or conical shape or configuration, and may instead have teeth height 33 which are shorter and do not extend past an exterior contact surface 48, but only extends partially into the end cap 40 or 42.

Figure 3A:
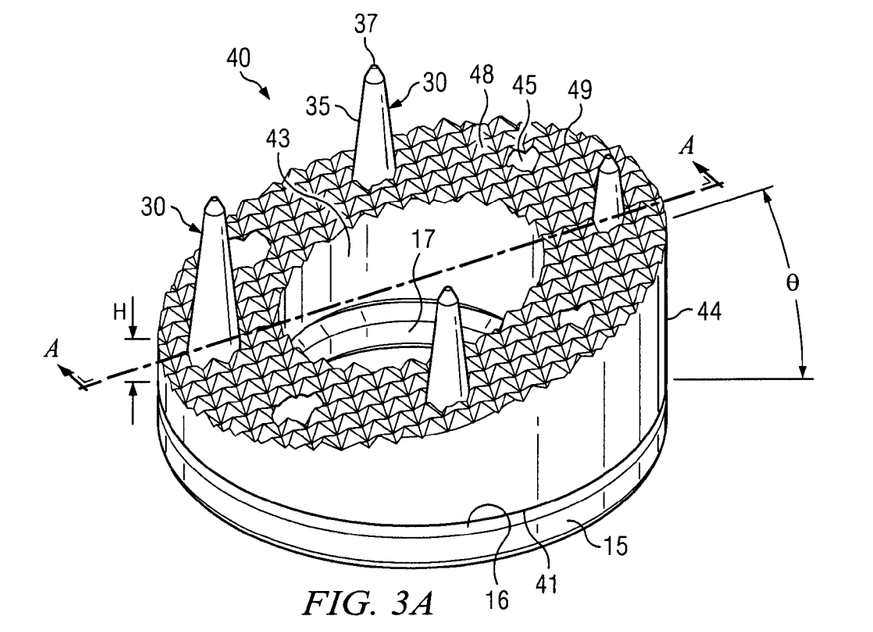
FIG. 3A is a perspective view of an implant base section with teeth engaging an end cap according to one embodiment.
Figure 3C:
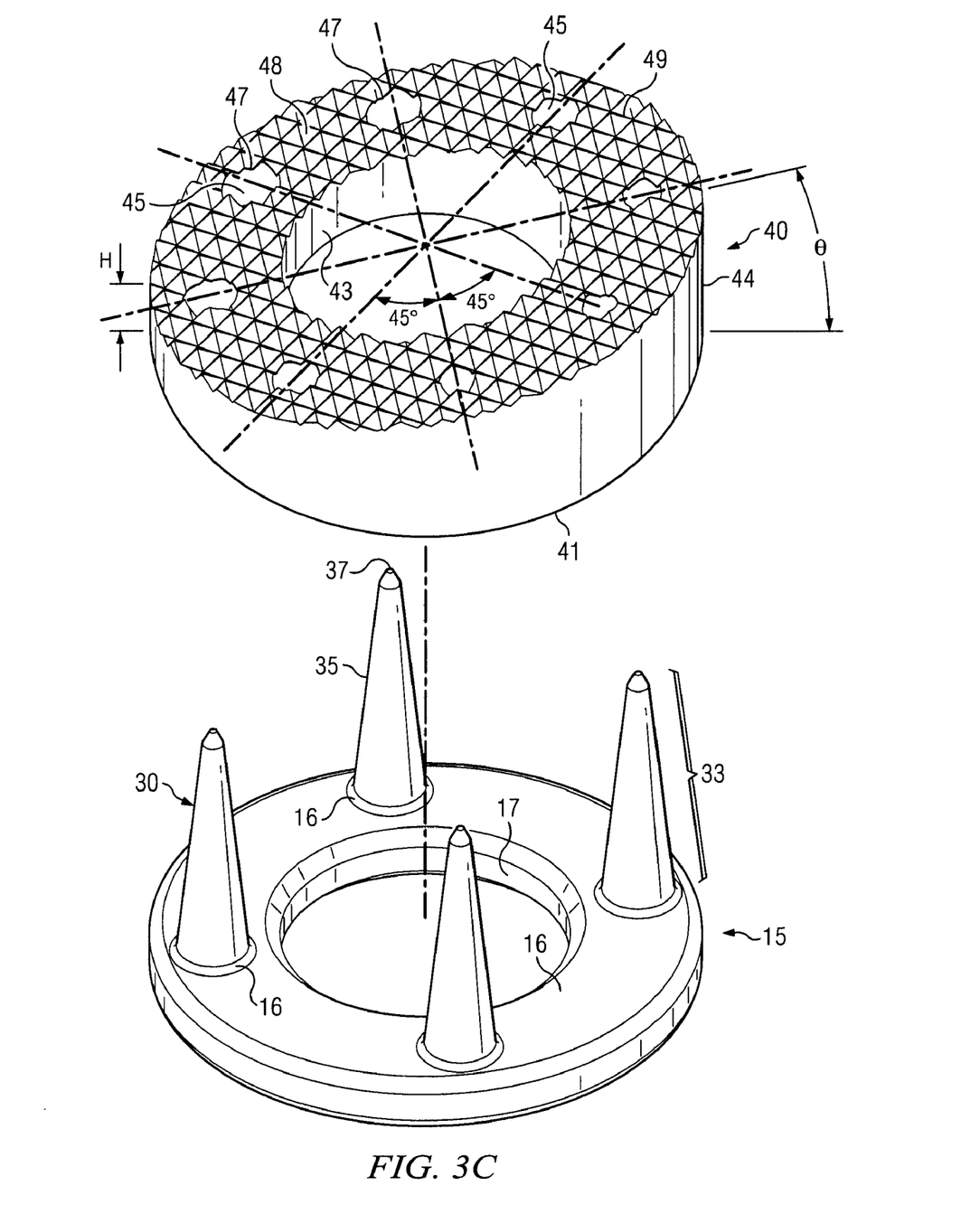
FIG. 3C is a perspective exploded view of the implant base section and end cap of FIG. 3A.
Figure 4:
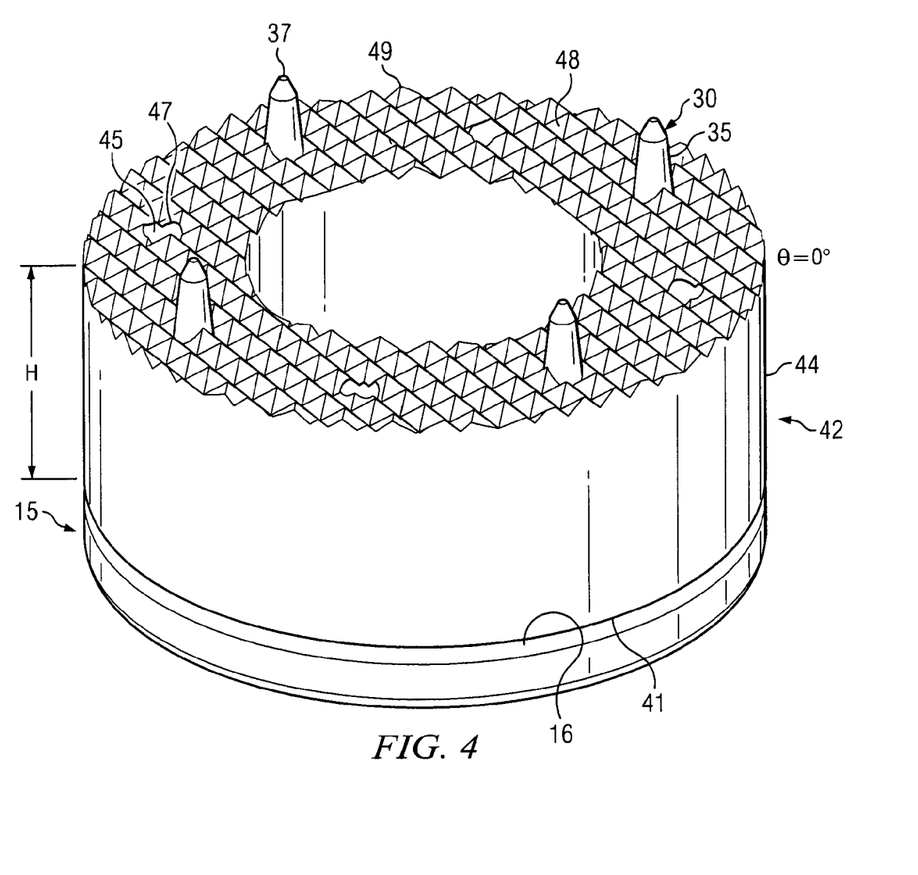
FIG. 4 is a perspective view of an implant base section with teeth engaging a Zero degree end cap according to one embodiment.

The implant base section 15 and 25 preferably have two or more extending base teeth 30 to accept and provide for a stable placement of an end cap 40 or 42 onto the implant base section 15 and 25, via engagement with corresponding locking apertures or passages 45 on the end cap 40 and 42. In one aspect shown in FIGS. 2A-4, the implant base section 15 and 25 will preferably have four tapered or cone-type base teeth 30 to accept the placement of an end cap 40 or 42 onto the implant base section 15 and 25. The base teeth 30 are positioned around the periphery of the exterior surface 16 and 26 of the first and second base section 15 and 25. Further, the base teeth 30 are preferably positioned evenly or equidistantly around the exterior surface 16 and 26, as best shown in FIGS. 2D & 3C. The base teeth 30 may also be located at non-equidistant locations around the exterior surface 16 and 26 as may be selected or required by a surgical procedure or clinical application, or surgeon need or selection. As will be discussed below, the number of base teeth 30 can be equal to or less than the number of end cap locking apertures 45 to permit placement of the end cap 40 or 42 onto the implant base section 15 and 25 via engagement between the base teeth 30 and corresponding locking apertures or passages 45, as shown in FIGS. 2A, 3A and 4. The base teeth 30, in addition to providing a mechanism to accept placement of the end cap 40 or 42 on the implant base section 15 and 25, also provide a securing and stabilizing function so that the end cap 40 or 42 can more securely rest on the implant base section 15 and 25. The greater the number of base teeth 30, the better the end cap 40 or 42 will sit on the implant base section 15 and 24.

Figure 3B:
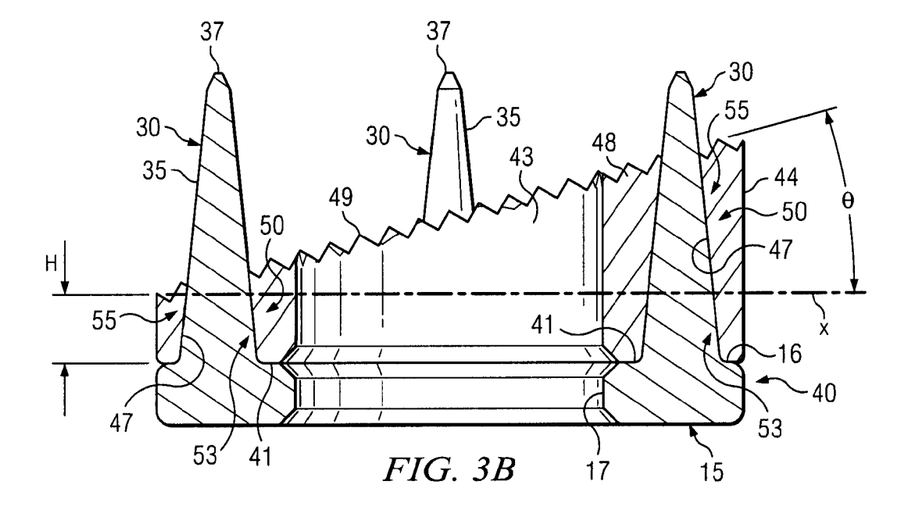
FIG. 3B is a section view along the line A-A of the implant base section and end cap of FIG. 3A.

The base teeth 30 preferably have a tooth height 33 that is taller than the exterior contact surface 48 of an end cap 40 or 42 as FIGS. 3A & 3B. In this manner, the base teeth 30 extend past the exterior end cap contact surface 48 sufficiently to penetrate, insert and embed into the adjacent end plate vertebral member 100 and 105. This aspect of the base teeth 30 provide stability for the expanded implant 10 and prevent the inserted implant 10 from being ejected out of the intervertebral space 101 after implant 10 insertion. The actual tooth height 33 will vary to accommodate the selection or need of a surgeon, medical procedure or clinical need. When the implant 10, with one or two caps 40 or 42, is inserted into an intervertebral space 101 and set to a desired implant height in the intervertebral space 101, via appropriate instruments (not shown), the protruding base teeth 30 will penetrate and insert into the adjacent end plate vertebral member 100 and 105 to maintain a stable implant 10 position between the adjacent vertebral members 100 and 105. Those of skill in the art will recognize that other teeth height 33 may be used depending on surgeon need, or procedure or clinical need.

For example, in an alternative embodiment, the base teeth 30 may instead have teeth height 33 which are shorter and extend partially into the end cap 40 or 42 body but do not extend past the exterior contact surface 48. The base teeth 30 could still maintain a tapered configuration and a substantially cone or conical shape or configuration. The implant base section would preferably have two or more extending base teeth 30 to accept and provide for a stable placement of an end cap 40 or 42 onto the implant base section 15 and 25, via engagement with corresponding locking apertures or passages 45 on the end cap 40 and 42. In such an embodiment, a corresponding end cap may have locking apertures which partially extend into the end cap 40 and 42 and are configured to accept the shorter base teeth. The implant base section 15 and 25 with the shorter base teeth will have two or more tapered or cone-type base teeth 30 to accept placement of an end cap 40 or 42 onto a complimentary implant base section 15 and 25. The greater the number of base teeth 30, the more securely the end cap 40 or 42 will sit on the implant base section 15 and 24. The shorter base teeth could also be positioned around the periphery of the exterior surface 16 and 26 of the first and second base section 15 and 25. And, would preferably be positioned evenly or equidistantly around the exterior surface 16 and 26, similar to the base teeth shown in FIG. 3C. The shorter base teeth may also be located at non-equidistant locations around the exterior surface 16 and 26 as may be selected or required by a surgical procedure or clinical application, or surgeon need or selection.

In this alternate embodiment, the shorter base teeth 30 preferably have shorter teeth height 33 which would extend partially into an end cap body and would not extend past the exterior contact surface 48 of the end cap. In this manner, the shorter base teeth provide a mechanism to accept locking placement of the end cap 40 or 42 onto the implant base section. The corresponding end cap may have one or more end cap teeth which assist in providing a securing and stabilizing function of the combined end cap and implant body. The end cap teeth may be a small number of large end cap teeth that extend from the end cap exterior surface 48 (for example similar in configuration to the base teeth 30 shown in FIGS. 3A & 3C) or may be a series of smaller end cap teeth 49 extending from the end cap exterior surface 48 as shown in FIGS. 3C and 4. The end cap teeth may also be a combination of large end cap teeth and a series of smaller end cap teeth 49 extending from the end cap exterior surface 48, similar to that shown in FIG. 3A, where the four large teeth would extend form the end cap exterior surface 48 instead of the implant base section.

In this aspect, the end cap includes end cap teeth which will come in contact with and engage the end plate of an adjacent vertebral body once the combined implant body and end cap are positioned in an intervertebral space 101 between vertebral members 100 and 105. The end cap teeth will provide a securing and stabilizing function of the combined end cap and implant body. The end cap teeth will extend from the end cap exterior surface 48 sufficiently to penetrate, insert and embed into the adjacent vertebral member 100 and 105 end plate. This end cap teeth aspect provides stability for the expanded implant 10 and prevents the inserted implant 10, that includes the implant body with shorter base teeth and end cap combination with gripping end cap teeth, from being ejected out of the intervertebral space 101 after implant 10 insertion. The actual end cap teeth height can vary to accommodate the selection or need of a surgeon, medical procedure or clinical need. When the implant 10 with shorter base teeth, with one or two caps 40 or 42 having end cap teeth, is inserted into an intervertebral space 101 and set to a desired implant height in the intervertebral space 101, via appropriate instruments (not shown), the protruding end cap teeth will penetrate and insert into the adjacent vertebral member 100 and 105 end plate to maintain a stable implant 10 position between the adjacent vertebral members 100 and 105.

FIG. 3A shows a perspective view of an implant base section 15 with base teeth 30 engaging an end cap 40 according to one embodiment. FIG. 3B is a section view along the line A-A of the implant base section 15 and end cap 40 of FIG. 3A. FIG. 3C is a perspective exploded view of the implant base section 15 and end cap 40 FIG. 3A. As discussed previously, the implant base section 15 is substantially flat and comprises base teeth 30 which extend away from an exterior surface 16 in a substantially vertical or axial direction. The base teeth 30 preferably have a tapered or substantially cone or conical shape or configuration 35. Those of skill in the art will recognize that other sizes, shapes and configuration may be used depending on medical procedure or clinical need, or surgeon need or selection. For example, the base teeth 30 may have shorter teeth height which would extend partially into a corresponding end cap body and not past the exterior contact surface 48 of the end cap. Such shorter base teeth may also have a tapered configuration and a substantially cone or conical shape or configuration.

The implant base section 15 preferably has four tapered base teeth 30 which are adapted to accept placement of the end cap 40 onto the implant base section 15. However, in alternate embodiments, the implant base section 15 may have two or more extending base teeth 30 to accept and provide for a secure and stable placement of an end cap 40 via engagement with corresponding locking apertures or passages 45 on the end cap 40. The base teeth 30 are preferably located equidistantly around the periphery of the exterior surface 16 of base section 15. The base teeth 30 preferably have the same teeth height 33. The base teeth 30 may have teeth height 33 which extend past the exterior contact surface 48 of a corresponding end cap exterior surface or which are shorter and only extend into the end cap body and not past the exterior contact surface 48, or a combination of these two types of shorter and longer base teeth. The base teeth 30 may also be positioned at non-equidistant positions around the periphery or other locations of the exterior surface 16, and/or have different teeth heights 33 as may be required by a surgical procedure or clinical application, or surgeon need or selection. The base teeth 30 also have a point, conical or other configuration which will enable the base teeth 30 penetrate and enter into an adjacent vertebral member 100 or 105 end plate. In this manner, when the base teeth 30 extend past the exterior contact surface 48 of a corresponding end cap, the base teeth 30 can more efficiently penetrate and embed into the adjacent end plate vertebral member 100 and 105 to provide implant 10 stability, and prevent implant 10 ejection from the intervertebral space 101. In a case where the base teeth 30 do not extend past the exterior contact surface 48 of a corresponding end cap, the extending base teeth would accept, and provide for stable placement of, an end cap 40 or 42 onto the implant base section via engagement of the shorter base teeth with corresponding and complimentary locking apertures or passages in an end cap 40 and 42. In this alternate embodiment, the end cap would include end cap teeth which will engage the end plate of an adjacent vertebral body once the combined implant body and end cap are positioned in an intervertebral space 101. The end cap teeth will extend from the end cap exterior surface 48 sufficiently to grip, penetrate, insert and embed into the adjacent vertebral member end plate to thereby provide implant stability in the intervertebral disc space 101 and prevent the inserted implant 10 from being ejected out of the intervertebral space 101.

The implant base section 15 also includes a base aperture 17 to receive or permit delivery of bone growth material into the implant 10 which will permit fusion once the implant is in place between the vertebral members 100 and 105. The base aperture 17 is preferably aligned with and has the same size as a corresponding end cap central aperture 43. Those of skill in the art will recognize that the base aperture 17 and end cap apertures may also be of different sizes and non-aligned if desired or needed by a surgeon, medical procedure or clinical application.

The end cap 40 comprises an annular-like shape with an exterior contact surface 48, locking apertures or passages 45, a seating surface 41, a substantially vertical exterior cap wall 44 and a central aperture 43. The exterior contact surface 48 and a seating surface 41 are bounded by the vertical exterior cap wall 44 and the central aperture 43. The contact surface 48 extends around the central opening 43. The contact surface 48 includes end cap teeth 49 which will engage the end plates of an adjacent vertebral member 100 or 105 to assist the implant 10 grip the vertebral member end plate, provide implant 10 stability in the disc space 101, and prevent implant 10 ejection from the intervertebral space 101. Those of skill in the art will recognize that the number, size, shape, orientation and spacing of the end cap teeth 49 may vary according to the needs of a medical procedure or clinical application.

In an embodiment where a corresponding implant base section has base teeth 30 that do not extend past the exterior contact surface 48 of the end cap, the end cap may have one or more end cap teeth which assist in providing a securing and stabilizing function of a combined end cap and implant body. The end cap teeth may comprise one or more large end cap teeth that extend from the end cap exterior surface 48 (similar in configuration to the base teeth 30 shown in FIG. 3A) or may be a series of smaller end cap teeth 49 extending from the end cap exterior surface 48 as shown in FIGS. 3C and 4. The end cap teeth may also be a combination of large end cap teeth and a series of smaller end cap teeth 49 extending from the end cap exterior surface 48, similar to that shown in FIG. 3A, where the four large teeth would extend form the end cap exterior surface 48 instead of the implant base section. In this aspect, the end cap teeth will engage the end plate of an adjacent vertebral body once the combined implant body and end cap are positioned in an intervertebral space 101. The end cap teeth will provide a securing and stabilizing function of a combined end cap and implant body. The end cap teeth will extend from the end cap exterior surface 48 sufficiently to grip, penetrate, insert and embed into the adjacent vertebral member 100 and 105 end plate to thereby provide implant stability in the intervertebral disc space 101 and prevent the inserted implant 10 from being ejected out of the intervertebral space 101 after implant 10 insertion. The actual end cap teeth height may vary to accommodate the selection or need of a surgeon, medical procedure or clinical need.

The seating surface 41 has a configuration that complements the exterior surface 16 of the implant base section 15 such that the end cap 40 can seat on the implant base section 15. In a preferred aspect, the seating surface 41 and the exterior surface 16 have complimentary and substantially flat surfaces such that the end cap 40 can seat flush on the implant base section 15. The central aperture 43 is preferably aligned with and the same size as the corresponding base aperture 17. Those of skill in the art will recognize that the central aperture 43 and base aperture 17 may also be of different sizes and non-aligned if desired or needed by a surgeon, medical procedure or clinical application.

The end cap further comprises an angulation θ aspect and an end cap vertex height H. The end cap angulation θ and cap height H may have a range of values as may be selected or needed by a surgeon, medical procedure or clinical application. In one aspect, preferred discrete values for end cap angulation are 0°, 4°, 8° and 15° degrees measured from an angulation reference line X, shown in FIG. 3B. In other embodiments, the preferred angulation θ values may be in the range of zero and thirty degrees (0°-30°), with a preferred range of between zero and fifteen degrees (0°-15°). In one aspect, the cap height H may have preferred values in 1.0 mm or 0.5 mm increments measured from the end cap seating surface 41. The angulation reference line X is preferably at the cap height H value as shown in FIG. 3B. The end cap's angulation θ is a measure of the exterior contact surface's 48 inclination relative to the angulation reference line X. Insertion of an implant 10 with an end cap 40 having an angulation θ aspect enables the end cap 40 to impart a desired or selected angulation θ to an adjacent vertebral member 100 or 105. In this manner, selective angulation θ can be imparted to the adjacent vertebral body 100 or 105 and thereby assist in the correction and/or improved orientation, stabilization and alignment of the spine. In the event where additional implant height H is desired or required without any angulation, an end cap 40 having angulation θ of 0° degrees may be used to impart the additional height to the implant 10 in the amount of an end cap height H. Such a case is illustrated in FIG. 4 which shows a perspective view of an implant base section 15 with an end cap 40 having angulation θ of 0° degrees and a certain cap height H.

The end cap 40 further comprises a series of locking apertures or passages 45 which enable placement and locking of the end cap 40 onto the implant base section 15 via engagement of the locking apertures 45 and corresponding extending base teeth 30. The end cap 40 locking apertures or passages 45 extend in a substantially vertical orientation between and through the contact surface 48 and seating surface 41. The locking apertures or passages 45 will have a complimentary configuration to that of the extending base teeth 30 which are inserted into the locking apertures 45 when the end cap 40 is positioned on the implant base section 15 and 25. As shown in FIG. 3B, the locking apertures or passages 45 preferably have a tapered or substantially cone or conical shape or configuration 47 which compliments and engages the tapered base teeth 30 upon placement of an end cap 40 onto the implant base section 15 or 25. Those of skill in the art will recognize that other sizes, shapes and configuration may be used for the locking apertures or passages 45 depending on medical procedure or clinical need, or surgeon need or selection, as long as they have a complimentary configuration with the base teeth 30 which permit insertion of and engagement with the extending base teeth 30 when the end cap 40 is positioned on the implant base section 15 and 25.

In an implant base section embodiment with shorter base teeth 30 that do not extend past the exterior contact surface 48 of the end cap is used, the end cap may comprise a series of locking apertures or passages which permit placement and locking of the end cap 40 onto the implant base section 15 via engagement of the locking apertures 45 and corresponding shorter base teeth 30. In this aspect, the end cap 40 locking apertures or passages 45 extend away from the seating surface in a substantially vertical orientation into the end cap body, and toward the exterior contact surface but do not extend to the exterior contact surface 48 of the end cap. The end cap 40 locking apertures or passages 45 extend to a point between the contact surface 48 and seating surface 41 to a length that will correspond to complimentary shorter base teeth which can be inserted into the locking apertures or passages 45. The locking apertures or passages 45 will also have a complimentary configuration to that of corresponding extending base teeth 30 which will be inserted into the locking apertures 45 when the end cap 40 is positioned on the implant base section 15 and 25. The locking apertures or passages 45 preferably have a tapered or substantially cone or conical shape or configuration 47 which will compliment and lockingly engage (via a tapered lock) the correspondingly tapered shorter base teeth 30 upon placement of an end cap 40 onto the implant base section 15 or 25. Those of skill in the art will recognize that other sizes, shapes and configuration may be used for the locking apertures or passages 45 depending on medical procedure or clinical need, or surgeon need or selection, as long as they have a complimentary configuration with the shorter base teeth which permit insertion of and engagement with the shorter base teeth when the end cap 40 is positioned on the implant base section 15 and 25.

In another aspect, the end cap 40 locking apertures or passages 45 may extend between and through the contact surface 48 and seating surface 41 when the shorter base teeth are used. In yet another aspect, the end cap 40 may have one or more locking apertures or passages 45 where at least one locking aperture extends to a point between the contact surface 48 and seating surface 41, and at least one locking aperture extends between and through the contact surface 48 and seating surface 41 when the shorter base teeth are used. In these aspects, the locking apertures or passages 45 will preferably have a complimentary configuration to that of corresponding extending base teeth 30 which will be inserted into the locking apertures 45 when the end cap 40 is positioned on the implant base section 15 and 25. The locking apertures or passages 45 preferably have a tapered or substantially cone or conical shape or configuration 47 which will compliment and lockingly engage (via a tapered lock) the correspondingly tapered shorter base teeth 30 upon placement of an end cap 40 onto the implant base section 15 or 25.

The locking apertures or passages 45 are located in an end cap area between the vertical exterior cap wall 44 and the central aperture 43, and between the vertical exterior cap wall 44 and the central aperture 43. Moreover, an end cap locking aperture or passage may extend between and through the contact surface 48 and seating surface 41, or may extend to a point between the contact surface 48 and seating surface 41, as discussed above, when shorter base section teeth are used. The end cap 40 preferably have at least the same number of locking apertures 45 as the number of extending base teeth 30 since the locking apertures or passages 45 accept entry of extending base teeth 30 when the end cap 40 or 42 is placed the implant base section 15 and 25. The locking apertures or passages 45 are preferably spaced and located evenly or equidistantly around the end cap area between the vertical exterior cap wall 44 and the central aperture 43. The spacing and location of the locking apertures 45 is selected to complimentarily align with the spacing and location of the base teeth 30 to permit end cap 40 insertion and engagement with the base teeth 30 of the implant base section 15 or 25. Those of skill in the art will recognize that the locking aperture or passages 45 may also be spaced or located at non-equidistant points around the end cap area between the vertical exterior cap wall 44 and the central aperture 43 as may be desired or required by a surgical procedure or clinical application, or surgeon need or selection. However, in the non-equidistant spacing or locating case, the locking apertures 45 must still be spaced and located to complimentarily align with the spacing and location of the base teeth 30 to permit end cap 40 insertion and engagement with the base teeth 30 of the implant base section 15 or 25.

As the locking apertures or passages 45 will accept entry of extending base teeth 30, the end cap 40 must have at least the same number of locking apertures 45 as the number of extending base teeth 30. If there are two extending teeth, then the there must be at least two locking apertures 45. If there are four extending teeth 30 (as is shown in FIGS. 2A-4), then there must be at least four locking apertures or passages 45 in order that the end cap 40 can be inserted and seated onto the implant base section 15. The end cap 40 may also have more locking apertures 45 than extending base teeth 30 on an implant base section 15 or 25. For example, as shown in FIGS. 2A-4, the end cap 40 has eight locking apertures or passages 45 while the base section 15 has four extending base teeth 30.

The locking apertures or passages 45 enable the end cap 40 to be selectively rotationally positioned or adjusted on the implant base section 15 or 25. The end cap 40 or 42 is rotationally adjustable relative to the implant body 20 and implant base section 15 or 25 about the longitudinal axis 5 of the implant body 20. The number of locking apertures 45 determine the number of positions or rotational positions at which the end cap 40 can be placed in or located on the implant base section 15 and 25. The greater the number of locking apertures 45 the larger the number of positions or rotational positions the end cap 40 can be adjusted and placed in or located on the implant base section 15 and 25. The more locking apertures or passages 45 there are, the greater degree of choice and control a surgeon will have in selecting a rotational position for the end cap 40 to be placed in or located on the implant base section 15 and 25. This aspect advantageously provides a surgeon selective control of where the end cap angulation θ and the end cap vertex height H will be rotational positioned on the implant base section 15 or 25. The ability to selectively position the end cap angulation θ permits a surgeon to determine where the end cap angulation θ and end cap height H will be applied or imparted to an the adjacent vertebral body 100 or 105. Prior to insertion of the implant 10 into the intervertebral disc space 101, the surgeon can decide where the end cap angulation θ and the end cap vertex height H are desired or needed for a particular medical procedure or clinical application.

As noted previously, a surgeon can selectively position the end cap 40 on the implant base plate 15 or 25 by rotating the end cap 40, either clockwise or counterclockwise, and then inserting the end cap locking apertures 45 onto the base teeth 30 at the desired or needed rotational position on the implant base plate 15. This aspect enables selective positioning of the end cap angulation θ which in turn permits the surgeon to decide where the end cap angulation θ and end cap height H will be applied or imparted to an the adjacent vertebral body 100 or 105. The clockwise or counterclockwise rotation of the end cap 40 moves or adjusts the end cap's 40 angulation θ and the end cap vertex height H relative to the implant base section 15 so as to position the end cap angulation θ and vertex height H at a desired or required point on the implant base section 15 or 25. For example at anterior, antereolateral, posterior or lateral points about the vertebral member 100 or 105, or vertebral disk space 101. This is in turn will position the end cap angulation θ and vertex height H at a desired or required point relative to the adjacent intervetebral member 100 or 105 once the implant 10 is inserted and positioned within the intervertebral space 101. The end cap 40 will then be able to impart desired or required angulation θ, orientation and vertex height H on the adjacent vertebral body at selected or required points on the adjacent vertebral body 100 or 105 to correct or improve the angulation, orientation, alignment and stabilization of the spine or spinal anatomy.

As noted above, the end cap 40 may be rotated so as to contact and impart angulation θ at different location points about the periphery of the adjacent vertebral body 100 or 105. The number of locking aperture or passages 45 impact the incremental degree of control, through clockwise or counterclockwise end cap 40 rotation, that a surgeon will have in selecting the end cap angulation θ position between the implant 10 and the adjacent vertebral body 100 or 105. In the embodiment shown in FIG. 3C, the end cap 40 has eight locking apertures 45 which are evenly or equidistantly space in the area between the contact surface 48 and seating surface 41. The equidistant spacing results in the locking apertures 45 being located and spaced apart from each other at about forty-five degrees (45°) around the end cap 40 as shown in FIG. 3C. In this embodiment then, the end cap 40 can be rotationally advanced, clockwise or counterclockwise, in single or multiple increments of forty-five degrees (45°) in order to rotationally position or reposition the end cap angulation θ position between the implant 10 and the adjacent vertebral body 100 or 105.

A greater degree of control in rotationally and incrementally advancing, clockwise or counterclockwise, the end cap 40 about the implant base section 15 may be obtained by increasing the number of locking apertures or passages 45. For example, if the end cap 40 were to have sixteen (16) locking apertures or passages 45 evenly or equidistantly spaced in the area between the contact surface 48 and seating surface 41. Then, equidistant and substantially circular spacing would result in the locking apertures or passages 45 being located and spaced apart from each other at twenty-two and a half degrees (22.5°) around the substantially circular area between the contact surface 48 and seating surface 41 of the end cap 40. In this case, the end cap 40 can be rotationally advanced, clockwise or counterclockwise, in single or multiple increments of twenty-two and a half degrees (22.5°) in order to position or reposition the end cap angulation θ position between the implant 10 and the adjacent vertebral body 100 or 105. The larger number of locking apertures or passages 45 provides a surgeon the ability to rotationally position or reposition the end cap 40 in smaller discrete increments. This greater degree of control provides the surgeon with more precise control on where the end cap angulation θ will be positioned between the implant 10 and the adjacent vertebral body 100 or 105. In this manner, the selected angulation θ and end cap vertex height H can be imparted to an adjacent vertebral member 100 or 105 to thereby impart or drive angular orientation and height adjustment of the adjacent vertebral member 100 or 105 for correction or improved alignment, angulation, orientation, and stabilization of the spine or spinal anatomy.

Once the appropriate or desired rotational position of the end cap 40 or 42 is obtained, the surgeon inserts or places the end cap 40 or 42 so that the end cap 40 engages and locks onto the implant base plate 15 or 25, as shown in FIGS. 3A & 3B. The locking of the end cap 40 onto the implant base plate 15 or 25 is accomplished through a connection or locking mechanism 50 where the locking apertures or passages 45 permit insertion of and engagement with corresponding and aligned base teeth 30 on the implant base plate 15 or 25. The locking apertures or passages 45 and the base teeth 30 have complimentary and opposing angled or tapered configurations 53 and 55 which result in the locking apertures or passages 45 and the bases teeth engaging to securely lock 50 the end cap 40 and the implant base plate 15 or 25. In this embodiment, the locking apertures or passages 45 preferably have a tapered configuration or a substantially cone, funnel or conical shaped passage 47 which complimentarily engages the tapered base teeth 30 upon placement of an end cap 40 onto the implant base section 15 or 25. When the end cap locking apertures or passages 45 are pressed onto the complimentary and aligned base teeth 30, as shown in FIGS. 3A & 3B, the resulting force experienced between the pressed adjacent tapered surfaces of the engaging locking passages 45 and base teeth 30 provides secure locking between the end cap 40 and the implant base plate 15 or 25. In this embodiment, such locking aspect is a taper locking mechanism 50.

The taper locking mechanism 50 sufficiently holds the end cap 40 or 42 on the implant base plate 15 or 25 to permit a surgeon to pre-assemble prior the end cap 40 or 42 to an implant 10 for insertion into an intervertrebal disc space 101. As long as there is a complimentary angled or tapered relationship 53 and 55 between the locking apertures or passages 45 and the base teeth 30, the end cap 40 and 42 and the implant base plate 15 or 25 will be securely locked together in place when the end cap 40 or 42 comes down on the base teeth 30 via a self-locking press fit arrangement, interference fit, flush friction fit arrangement, friction fit or compression fit. Those of skill in the art will recognize that other sizes, shapes and configurations may be used for the locking apertures and passages 45 and base teeth 30 to form the locking mechanism 50 depending on medical procedure or clinical need, or surgeon need or selection, so long as they have complimentary configurations and physical arrangements which permit insertion of and locking engagement between the locking apertures and passages 45 and base teeth 30 when the end cap 40 is positioned on the implant base section 15 and 25.

The implants 10 and end caps 40 or 42 may be implanted within a living patient for the treatment of various spinal disorders. The implant 10 may also be implanted in a non-living situation, such as within a cadaver, model, and the like. The non-living situation may be for one or more of testing, training, and demonstration purposes.

The end caps disclosed in this disclosure are preferably comprised of biocompatible materials substrates which can be used in combination with implants or devices configured to be inserted into an intervertebral space and contact against adjacent vertebral members. The biocompatible material substrate may include, among others, polyetheretherketone (PEEK) polymer material, homopolymers, co-polymers and oligomers of polyhydroxy acids, polyesters, polyorthoesters, polyanhydrides, polydioxanone, polydioxanediones, polyesteramides, polyaminoacids, polyamides, polycarbonates, polylactide, polyglycolide, tyrosine-derived polycarbonate, polyanhydride, polyorthoester, polyphosphazene, polyethylene, polyester, polyvinyl alcohol, polyacrylonitrile, polyamide, polytetrafluorethylene, poly-paraphenylene terephthalamide, polyetherketoneketone (PEKK); polyaryletherketones (PAEK), cellulose, carbon fiber reinforced composite, and mixtures thereof. The biocompatible material substrate may also be a metallic material and may include, among others, stainless steel, titanium, nitinol, platinum, tungsten, silver, palladium, cobalt chrome alloys, shape memory nitinol and mixtures thereof. The biocompatible material used can depend on the patient's need and physician requirements.

While embodiments of the invention have been illustrated and described in the present disclosure, the disclosure is to be considered as illustrative and not restrictive in character. The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant for insertion into an intervertebral space between a first and second vertebral member, the implant comprising:
    an implant body with at least one base section, the base section including base teeth, the base teeth comprise a tapered configuration; and
    an end cap adapted for selective positioning at a selected point on a base section, the end cap comprising
    an exterior contact surface that faces away from the implant body when the end cap is positioned on the base section,
    a seating surface adapted to contact the base section when the end cap is positioned on the implant body,
    an end cap angulation, and
    locking passages comprising a tapered passage configuration adapted to accept the base teeth, the locking passages extending between the exterior contact surface and the seating surface and adapted to receive base teeth, the locking passages and base teeth complimentarily configured to engage and securely maintain the end cap positioned on the base section;
wherein the implant imparts the end cap angulation to an adjacent vertebral body at the selected point when the implant is positioned in the intervertebral space;
wherein the base teeth and locking passages have opposing and complimentary configurations that together provide a locking engagement when the end cap is positioned on the base section.

2. The implant of claim 1, wherein the end cap is selectively positioned on the base section via rotational adjustment of the end cap about an implant longitudinal axis so that the end cap angulation coincides to the selected point.

3. The implant of claim 1, wherein the end cap angulation comprises an angular value in the range of between zero degrees to fifteen degrees (0°-15°).

4. The implant of claim 1, wherein the end cap angulation is an angular value selected from the group consisting of 0°, 4°, 8° and 15°.

5. The implant of claim 1, wherein the end cap further comprises an end cap height measured relative to the seating surface which enables the implant to both impart end cap height and end cap angulation to the adjacent vertebral body at the selected point.

6. The implant of claim 1, wherein the locking engagement is interference fit, a compression fit, a friction fit or a press fit.

7. The implant of claim 1, wherein the locking passages are spaced and located to enable complimentarily alignment with the base teeth to permit the end cap to be inserted onto the base section.

8. The implant of claim 7, wherein the locking passages are spaced and located equidistantly about the end cap.

9. The implant of claim 1, wherein one or more base teeth extend past the exterior contact surface when the end cap is positioned on the base section.

10. An end cap adapted for use with an implant having an implant body with at least one base section and base teeth, the end cap comprising:
    an exterior contact surface;
    a seating surface;
    a substantially vertical exterior cap wall extending between the exterior contact surface and the seating surface; and
    a plurality of locking passages comprising a tapered passage configuration adapted to accept the base teeth, the locking passages extending between the exterior contact surface and the seating surface, the locking passages configured to receive complimentarily configured base teeth to thereby engage and securely maintain the end cap positioned on the base section of the implant, wherein the base teeth comprise a tapered configuration;
    wherein the locking passages enable the end cap to be selectively positioned at a selected point on the implant base section;
    wherein the end cap positioned on the implant imparts an end cap angulation to an adjacent vertebral body at the selected point when the implant is positioned in an intervertebral space;
    wherein the base teeth and locking passages have opposing and complimentary configurations that together provide a locking engagement when the end cap is positioned on the base section.

11. The end cap of claim 10, wherein the end cap further comprises an end cap height measured relative to the seating surface which enables the end cap positioned on the implant to both impart end cap height and end cap angulation to the adjacent vertebral body at the selected point.

12. The end cap of claim 10, wherein the end cap is selectively positionable on the base section via rotational adjustment of the end cap about an implant longitudinal axis so that the end cap angulation coincides to the selected point.

13. The end cap of claim 10, wherein the end cap angulation comprises an angular value in the range of between zero degrees to fifteen degrees (0°-15°).

14. An end cap adapted for use with an implant having an implant body with at least one base section and base teeth, the end cap comprising:
    an exterior contact surface including end cap teeth extending away from the exterior contact surface;
    a seating surface adapted to contact the base section when the end cap is positioned on the implant body,
    a substantially vertical exterior cap wall extending between the exterior contact surface and the seating surface; and
    a plurality of locking passages comprising a tapered passage configuration adapted to accept the base teeth, the locking passages extending from the seating surface into the end cap toward the exterior contact surface and adapted to receive base teeth, the locking passages configured to receive complimentarily configured base teeth to thereby engage and securely maintain the end cap positioned on the base section of the implant, wherein the base teeth comprise a tapered configuration;
    wherein the locking passages enable the end cap to be selectively positioned at a selected point on the implant base section;
    wherein the end cap positioned on the implant imparts an end cap angulation to an adjacent vertebral body at the selected point when the implant is positioned in an intervertebral space,
    wherein the base teeth and locking passages have opposing and complimentary configurations that together provide a locking engagement when the end cap is positioned on the base section.

15. The end cap of claim 14, wherein the end cap further comprises an end cap height measured relative to the seating surface which enables the end cap positioned on the implant to both impart end cap height and the end cap angulation to the adjacent vertebral body at the selected point.

16. The end cap of claim 14, wherein the end cap is selectively positionable on the base section via rotational adjustment of the end cap about an implant longitudinal axis so that the end cap angulation coincides to the selected point.

17. The end cap of claim 14, wherein the end cap angulation comprises an angular value in the range of between zero degrees to fifteen degrees (0°-15°).

* * * * *